United States Patent [19]
Harris et al.

[11] Patent Number: 5,599,913
[45] Date of Patent: Feb. 4, 1997

[54] CHROMOIONOPHORES, OPTICAL SENSORS CONTAINING THEM AND A METHOD FOR DETERMINING THE PRESENCE OF ALKALI METAL CATIONS OR OF A BASE

[76] Inventors: Stephen J. Harris, 10 Broadford Crescent, Ballinteer, Dublin 16; Dermot Diamond, Coolquoy, The Ward, County Dublin, both of Ireland; Michael A. McKervey, 27a Osborne Park, Belfast BT9 6JN, Northern Ireland, United Kingdom

[21] Appl. No.: 381,912
[22] PCT Filed: Aug. 6, 1993
[86] PCT No.: PCT/IE93/00046
§ 371 Date: Mar. 28, 1995
§ 102(e) Date: Mar. 28, 1995
[87] PCT Pub. No.: WO94/04483
PCT Pub. Date: Mar. 3, 1994

[30] Foreign Application Priority Data

Aug. 12, 1992 [IE] Ireland .................................. S922577

[51] Int. Cl.⁶ ..................... C07C 205/42; C07C 205/43; C07C 205/45; C07C 245/08; G01N 31/22
[52] U.S. Cl. .............................. 534/856; 435/808; 436/43; 436/111; 436/112; 534/852; 534/859; 560/57; 560/58; 568/387
[58] Field of Search ....................................... 534/856, 852, 534/859; 560/57, 58; 568/337; 435/808; 436/112, 111, 43

[56] References Cited

PUBLICATIONS

F. Arnaud–Neu et al. II, "Selective Alkali–metal Cation Complexation by Chemically Modified Calixarenes", J. Chem. Soc., 1992, pp. 1119–1125.
I. Aoki et al., "A New Metal Sensory System Based on Intramolecular Fluorescence Quenching on the Ionophoric Calix[4]arene Ring", J. Chem. Soc. 1992, pp. 730–732.
F. Arnaud–Neu et al. I, "Synthesis, X–ray Crystal Structures, and Cation–Binding Properties of Alkyl Calixaryl Esters and Ketones, a New Family of Macrocylic Molecular Receptors", J. Am. Chem. Soc., 1989, vol. 111, pp. 8681–8691.
N. Sato et al., "Energy–transfer Luminescence of Lanthanide Ions Encapsulated in Sensitizer–modified Calix[4]–arenes", J. Chem. Soc., 1993, pp. 621–624.
D. Cram et al., "Host–Guest Complexation. 45. A Highly Preorganized Chromogenic Spherand Indicator System Specific for Sodium and Lithium Ions", J. Am. Chem. Soc., 1988, vol. 110, pp. 571–577.
R. Helgeson et al., "Host–Guest Complexation, 50. Potassium and Sodium Ion–Selective Chromogenic Ionophores", J. Am. Chem. Soc., 1989, vol. 111, pp. 6339–6350.
H. Shimizu et al., "Chromogenic Calix[4]arene", Chemistry Letters, 1991, pp. 2147–2150.
R. Forster et al., "Calixarenes as Active Agents for Chemical Sensors", Sensors and Actuators, 1991, vol. 4, pp. 325–331.
A. Cadogan et al., "Sodium–selective Polymeric Membranes Electrodes Based on Calix[4]arene Ionophores", Analyst, 1989, vol. 114, pp. 1551–1554.
Y. Nakamoto et al., "Synthesis and Properties of Chromogenic Calixarene", Workshop on Calixarenes and Related Compounds, Aug. 28–30, 1991, 3 pages.
I. Aoki et al. II, "Fluorescent Calix[4]arene which responds to Solvent Polarity and Metal Ions", J. Chem. Soc., 1991, pp. 1771–1773.
A. King et al., "A Highly Selective Chromoionophore for Potassium Based upon a Bridged Calix[4]arene", J. Chem. Soc., 1992, pp. 582–584.
M. Egashira et al., "Enhancement of Trimethylamine Sensitivity of Semiconductor Gas Sensors by Ruthenium", Chemistry Letters, 1988, pp. 389–392.
K. Nakashima et al., "Coloration Reaction of a Crowned 2,4–Dinitropheylazophenol—Barium (II) Complex with Amines and Its Application to Flow Injection Spectrophotometry", Analysis, Apr. 1989, vol. 114, pp. 501–504.

*Primary Examiner*—Floyd D. Higel
*Attorney, Agent, or Firm*—Young & Thompson

[57] ABSTRACT

New chromoionophores of the formula IV

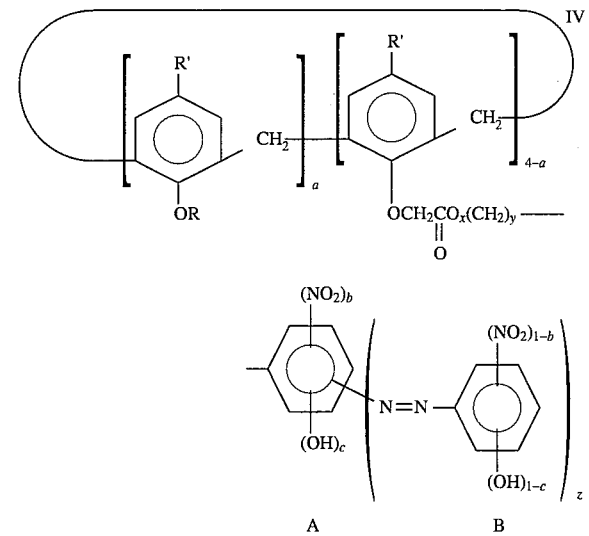

wherein
  $a=0-3$, $b=0$ or $1$, $c=0$ or $1$, $x=0$ or $1$, $y=0$ or $1$, $z=0$ or $1$,
  R', which may be the same or different in each aryl group, is H, halogen, hydrocarbyl, aryl, hydrocarbylaryl or a substituted derivative thereof;
  R, which may be the same or different, is hydrocarbyl, aryl, hydrocarbylaryl, or a substituted derivative thereof
are useful in optical sensors or colourmetric reagents for clinical use particularly for lithium, When complexed with lithium, the chromoionophores of the invention and other calixarene derivatives can be used for detecting amines, particularly trimethylamine, as an indicator of fish spoilage.

16 Claims, 7 Drawing Sheets

CHROMOIONOPHORES, OPTICAL SENSORS CONTAINING THEM AND A METHOD FOR DETERMINING THE PRESENCE OF ALKALI METAL CATIONS OR OF A BASE

This application is a 371 of PCT/IE93/00046 filed Aug. 6, 1993.

TECHNICAL FIELD

This invention relates to novel chromogenic ligands based on tetrameric calixarenes, and to the use of these ligands in optical sensors, or colourimetric reagents, particularly for medical use in the determination of lithium, or for the detection of amines in the food industry.

BACKGROUND ART

There is increasing interest in the development of optical sensors, particularly for medical use in the determination of clinically important species. Sensors for sodium, potassium and lithium have proven particularly difficult to develop, in view of the limited complexation of these ions with known chromogenic ligands. Some success has been reported in recent years with chromogenic crown ethers, spherands and cryptands (1, 2, 14). It has been demonstrated that attachment of ionisable chromogenic groups in positions adjacent to the polar cavity of these molecules can produce materials which show striking changes in absorbtion on complexation. Incorporation of a metal cation into the cavity is accompanied by deprotonation and it is the latter process that produces the optical reponse.

Certain calixaryl compounds have been shown to be efficient ionophores for alkali metal cations and have been used to produce ion-selective electrodes for sodium, potassium and caesium (7,8). Chromogenic calixarenes have also been described: Shimizu et. al (3) described an ion-selective chromogenic calixarene of the formula I:

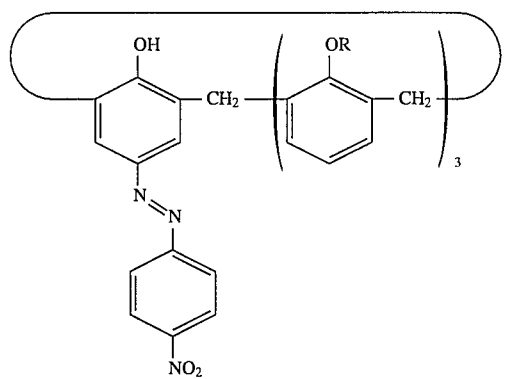

R = CH$_2$CO$_2$Et

This derivative has within the molecule both the triester moiety as a metal-binding site and the azophenol moiety as a colouration site. It was described as having good lithium selectivity. Nakamoto et. al (11) described an azocalixarene of the formula II

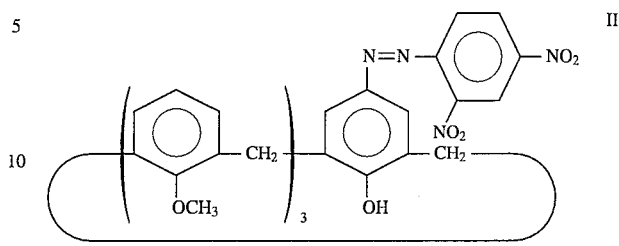

This compound showed a lithium specific colour change. King et. al. (19) described chromoionophores of the formula IIa.

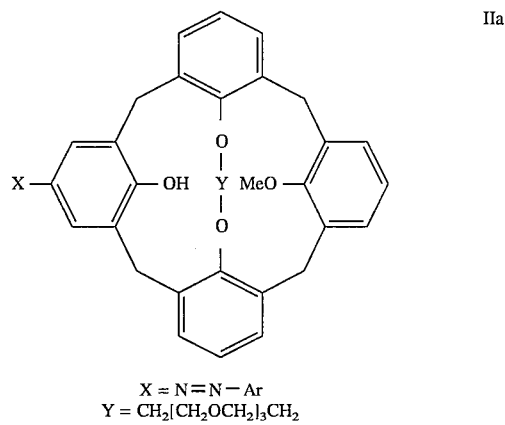

X = N=N—Ar
Y = CH$_2$[CH$_2$OCH$_2$]$_3$CH$_2$

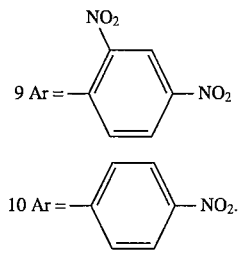

These compounds showed a potassium specific colour change.

However the azocalixarenes of formula II and II a having the azo groups directly attached to a calixarene aryl group are relatively difficult to synthesise and require long preparation routes with relatively low yields.

Fluorescence spectrophotometric determination has also been investigated for metal ion analysis. Fluoro-ionophores of cyclic and non-cyclic polyethers (4,5), and, more recently, of a calix(4)arene (6), have been synthesized and reported to produce a marked increase in fluorescence in the presence of lithium ions in the case of the former, and sodium ions in the latter.

Aoki et. al (12) described a fluorescent calixarene of the formula III

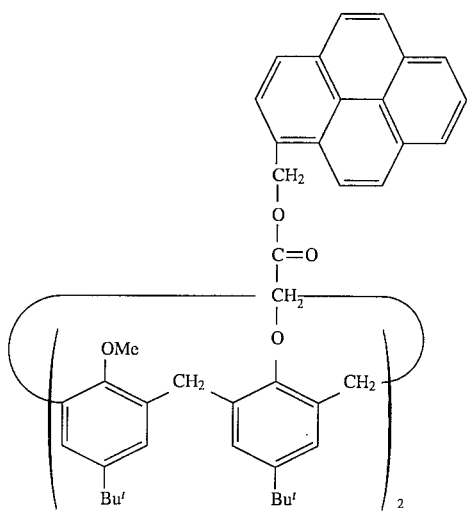

However this is not a chromoionophore.

Calixarenes having chromogenic moieties have also been described since the priority date of this application by Kubo et al (18).

There is also a need for a non-instrumental detector of volatile amines such as trimethylamine (TMA). TMA is a degradation product of the reaction of bacteria such as *Pseudomonas* upon trimethylamine oxide in marine fish after death[20]. Its detection along with other amines, has been used as a means of determining fish freshness. Traditionally fish freshness has been assessed by olfactory analysis[21] but this is both time consuming and expensive. Colorimetric methods have also been employed and developed successfully, and can distinguish between TMA and dimethyl amine (DMA)[22-24], both of which are generated (along with other volatile amines and sulphides) as the fish spoils[20]. However, these methods require time-consuming mincing of the fish followed by solvent extraction before analysis. More recently Gastec detector tubes containing crystals which change colour as they react with a specific gas or vapour have been developed and used in amine analysis of the gill air of fish[25] with amines being determined in a concentration range of 0.05 to 5 ppm. These tubes are attached to a pump and a specific volume of gas is analysed. GC anaylsis of amines produced by fish has also been used to distinguish between TMA and DMA and to quantify the levels at which each are present[26]. Another approach investigated for TMA analysis involves the use of semiconductor gas sensors containing ruthenium. Such sensors were found to respond well to 50 ppm TMA and were used to determine the freshness of Japanese saurel[27-28]. All of these methods, while not all destructive, do involve a certain degree of handling of the samples or involve some form of instrumentation. The development of a non-instrumental indicator system which would respond quickly to gaseous amines could obviously be of benefit to the food industry.

Nakashima et al (29) described a crowned 2, 4-dinitrophenylazophenol which, when complexed with $Ba^{2+}$, could be used for detection of volatile amines such as trimethylamine in a flow-injection analysis (FIA system).

DISCLOSURE OF INVENTION

The present invention provides new chromoionophores of the formula IV

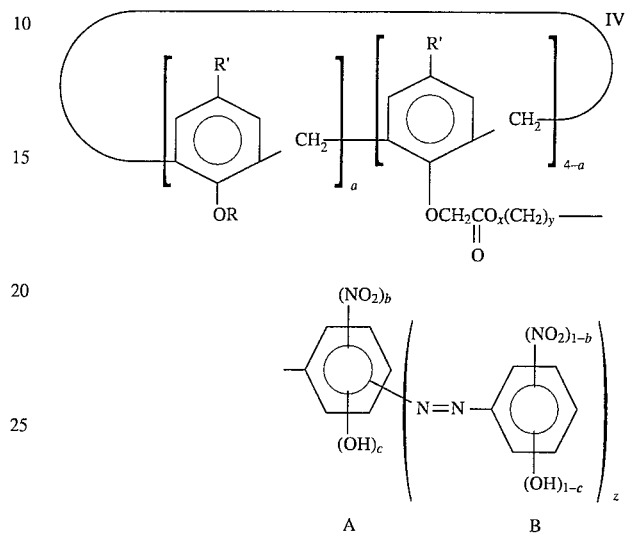

wherein
a=0–3,
b=0 or 1,
c=0 or 1,
x=0 or 1,
y=0 or 1,
z=0 or 1,
provided that when z=0,b=c=1, R' which may be the same or different in each aryl group, is H, halogen, hydrocarbyl, aryl, hydrocarbylaryl or a substituted derivative thereof;

R, which may be the same or different, is hydrocarbyl, aryl, hydrocarbylaryl, or a substituted derivative thereof. Preferably R is

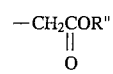

wherein R" is H, hydrocarbyl, aryl, hydrocarbylaryl or a substituted derivative thereof, In an alternative embodiment R is alkenyl, particularly —CH$_2$ CH=CH$_2$.

The aryl groups A and B may be additionally substituted with one or more further nitrogroups and/or with other electron withdrawing groups which have strong absorbance in the UV region and which do not interfere with proton removal from the —OH group.

A preferred group of chromoionophores is of the formula V:

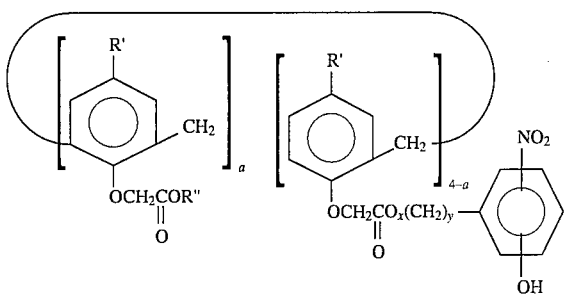

wherein a, x, y, R' and R" are as defined for formula IV.

Preferably the nitrophenol group is of the formula VI

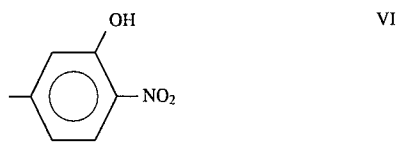

A further preferred group of chromoionophores of longer wavelength is of formula VII:

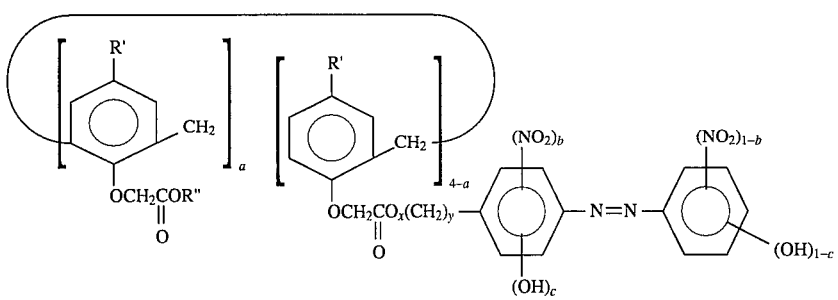

wherein a, b, c, x, y, z, R' and R" are as defined for formula IV.

Preferably in each of the formulae IV, V and VII x=y=1 and/or a=0 or 3.

The term "hydrocarbyl" as used herein means aliphatic hydrocarbyl including alkyl, alkenyl and alkynyl. Hydrocarbyl groups shall preferably contain from 1 to 20 carbon atoms, more preferably from 1 to 5 carbon atoms, and aryl and hydrocarbylaryl groups shall preferably have from 6 to 20 carbon atoms, more preferably from 6 to 10 carbon atoms. Hydrocarbyl groups are preferred, especially alkyl or alkenyl groups.

A substituted derivative of the foregoing may suitably be substituted with one or more halo groups or radicals containing nitrogen or substituted or interrupted by one or more oxo groups. Radicals containing nitrogen may or may not form part of a heterocyclic ring; a suitable radical may contain an amino or amide group, or may be a heterocyclic ring which may be saturated or unsaturated, aliphatic or aromatic, for example a 5- or 6-membered ring containing 1 or 2 nitrogen atoms. For analogous substituted compounds reference is directed to U.S. Pat. No. 4,882,449 Harris, the contents of which are incorporated herein by reference. Halogen may be chlorine, bromine, fluorine or iodine.

The azocalixarenes of Shimizu et. al (3) and Nakamoto et. al (11) were para-substituted to the calixarene phenolic group whereas the compounds of the present invention are substituted esters or ketones on one or more of the calixarene phenolic —OH groups. The compounds of the invention are easier to synthesise, using readily available starting materials and shorter routes.

The preparation of calixarene derivatives is known and is described, for example in C. Gutsche et. al., Acc. Chem. Res., 16, 161–170 (1983); in U.S. Pat. Nos. 4,556,700 Harris et. al., 4,866,198 Harris, 4,882,449 Harris and 5,132,345 Harris et. al., and in J. Inclusion Phenomena 2 199–206 (1984) D. Reidel Publishing Company; the appropriate disclosures of all of which are incorporated herein by reference. The preparation of aryl calixarene derivatives is described in EP 0,259,016. Mixed functionality calixarene derivatives are described in European Patent Publication No. 0,196,895 A2 and U.S. Pat. No. 4,642,362 Harris et. al. When a is greater than or equal to 2 in the compounds of formula IV, the aryl groups having the —OR side chain may be interspersed around the ring between the aryl groups having the chromogenic side chain.

The compounds of the present invention wherein x−y=1 may be prepared by reaction of the appropriate calixarene acid chloride with the appropriately nitro-substituted benzyl alcohol, which may be an azo derivative of the benzyl alcohol. The compounds of the invention wherein x=o may be prepared by reaction of the appropriate parent-calixarene having phenolic functionality with a halocetyl derivative of the appropriately nitro-substituted aryl group, following the procedure described for the preparation of calixarene ketone derivatives in U.S. Pat. No. 5,132,345.

Calixarene derivatives may usefully be polymer-bound by methods described in U.S. Pat. No. 4,642,362 Harris et. al., or 4,699,966 Harris et. al., or be methods analogous to those described for crown ethers in U.S. Pat. No. 4,447,585 Parker or Tetrahedron 36 461–510 (1980). The derivatives may also be silica gel bound by methods analogous to those described in J. Incl. Phenomena 7 127–136 (1989) or J. Chem. Soc. Chem. Comm. 812 (1988).

In the presence of alkali-metal ions and a base, a proton comes off the nitrophenol hydroxy group, causing a colour change. The compounds display a metal-selective shift in absorbance maximum from the UV into the visible region on addition of lithium ions and, to a lesser extent, sodium ions. Addition of the metal salt in the presence of a base is accompanied by a colour change from colourless to yellow in the case of nitrophenol—substituted compounds and yellow to red in the case of nitrophenylazophenol—substituted compounds, the colour density being concentration dependent.

The compounds of the present invention have potential uses in optical sensors, such as optical fibre cation sensors or colourimetric ion-selective electrodes, or in colourimetric reagents. The term optical sensor as used herein also includes an optical detector. In one aspect, the invention provides an optical sensor comprising a chromoionophore of the formula IV as defined above on a suitable carrier. In an ion-selective electrode, the supporting matrix is preferably poly(vinychloride)(PVC). Other polymeric materials such as silicon polymers may be used, see "Ion-Selective Electrode Reviews", Vol. 5, 1983, p 3–90, D. Ammann et. al.

The invention also provides an analytical method which comprises contacting a sample containing alkali metal ions with an optical sensor as defined above in the presence of a base.

The reaction can be represented by the following generalised equation:

$$LCH_{(m)} + M^+_{(aq)} + B_{(m)} \leftrightarrow LM^+C^-_{(m)} + BH^+_{(m)}$$

where $LCH_{(m)}$=ionisable chromoionophore in membrane phase;

$M^+_{aq}$=target ion in aqueous phase;

$B_{(m)}$=Base in membrane phase.

The invention further relates to use of an optical sensor as defined above in the presence of a base for determining alkali metal cations, particularly lithium.

In another aspect, the invention provides an optical sensor as defined above wherein the chromoionophore is complexed with an alkali metal cation, particularly lithium. The invention further relates to use of an optical sensor as defined in the preceding sentence for determining the presence of a base, particularly an amine such as triethylamine. In another definition, the invention provides a method for detecting the presence of a base which comprises locating an optical sensor as defined in this paragraph in an environment (such as food packaging) where the presence of a particular base is anticipated.

In one embodiment the invention provides a complex of a chromogenic calixarene of formula IV and a lithium salt for example $LiClO_4$. Other lithium salts may also be used.

Such a complex has been found to be capable of detecting trimethylamine:

(i) down to 0.45 ppm trimethylamine in solution;

(ii) when the complex is immobilised on a carrier such as filter paper down to 0.02 ppm gaseous trimethylamine; and (iii) when the complex is immobilised on a carrier such as filter paper sealed in gas-permeable plastics film, down to 2.5 ppm gaseous trimethylamine.

This aspect of the invention has potential advantages for the detection of food spoilage, particularly fish spoilage, as compared to existing methods, especially with regard to ease and simplicity of operation, speed and sensitivity of detection.

This aspect of the invention is not limited to the use of the calixarene derivatives of formula IV, although they are preferred over other chromogenic calixarene derivatives as described in the prior art references 3, 11 and 19 for reasons already explained. The present invention therefore extends to use of a complex of chromogenic calixarene derivative and a metal salt for detecting the presence of a base, particularly an amine such as triethylamine.

MODES FOR CARRYING OUT THE INVENTION

The invention is illustrated in the following Examples:

EXAMPLE 1

Preparation—Ligand I (formula VIII)

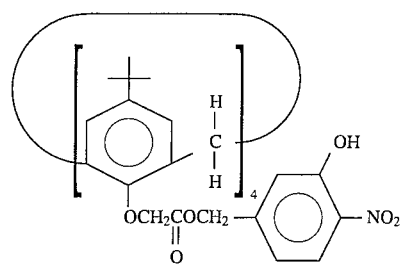

VIII

To 3.3 g (0.00375 mole) tetra p.tert.butyl calix(4)arene tetraacetic acid prepared as in EP 0 237 265 Harris assigned to Loctite (Ireland) Limited was added 10 mls thionyl chloride and the entire was stirred under reflux under nitrogen for 2 hours. All volatiles were then removed, the last traces under reduced pressure, to give 3.6 g colourless tetraacetyl chloride.

1.2 g (0.00122 mole) of this compound was dissolved in 5 mls dry THF under nitrogen to which was added 0.93 g (0.0055 mole) 3-hydroxy-4-nitrobenzyl alcohol from Aldrich Chemical Co. and 0.76 ml (0.0055 mole) triethylamine in 5 mls dry THF with stirring. The dark green brown reaction mixture was then allowed to stir for 24 hours at room temperature, after which all volatiles were removed, then taken up into 25 mls. dichloromethane which was washed twice with water to give after drying with dried magnesium sulphate 1.71 g (95%) yield brown solid product. The crude product was dissolved in 50 mls chloroform to which was added two spatula tipfuls of decolourising charcoal and the entire solution was boiled for five minutes, then filtered hot to give solid pale yellow solid which was purified by column chromatography on silica using 5% 40°–60° C. petroleum ether/dichloromethane to give 1.1 g (65%) very pale yellow pure tetraester mp 76°–8° C. i.r. Spectroscopy results: v 1756 (S) C=0 $cm^{-1}$ Elemental analysis results (calculated for $C_{80} H_{84} N_4 O_{24}$: C=64.67, H 5.70, N=3.79. Found C=64.04, H=5.75, N=3.35%).

The compound (Formula VIIIa):

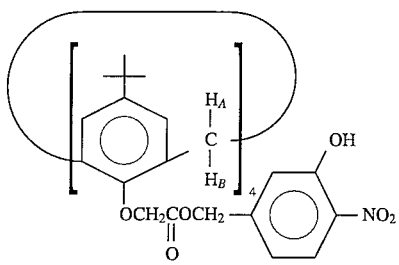

VIIIa is in distorted cone conformation, as shown by resonances in $^1H$ NMR $CDCl_3$ RT.

0.84 S (singlet) 18 H Area, 1.34 S 18 H Area. ppm. Upon complexation with NaSCN they collapse to one S 36 H 1.09 ppm.

$H_{AB}$: $H_B$ 3.30 doublet of doublets=4 H area ppm. $H_A$ 4.98 (doublet) d, 5.13 d=4 H area ppm.

Modified
AB quartet
pattern

EXAMPLE 2

Preparation—Ligand 2 (formula IX—monochromogenic)

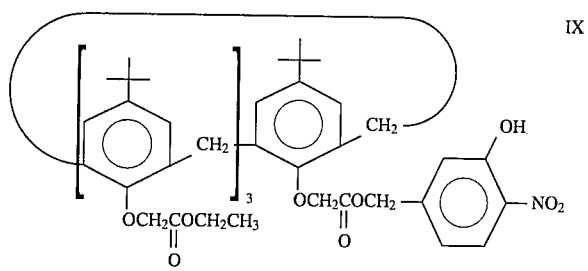

To 2.9 g (0.0031 mole) of compound X

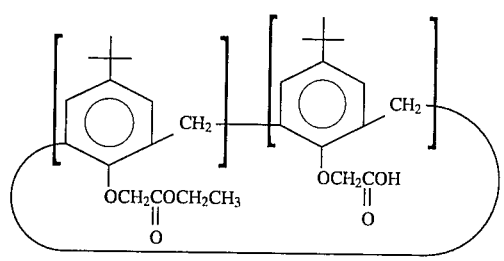

prepared as described in EP 0 432 990 A2 Harris et. al. assigned to Loctite (Ireland) Limited was added 10 mls thionyl chloride under nitrogen and the entire was refluxed for 2 hours following which all volatiles were removed under reduced pressure to give 3.0 g of the triester mono acid chloride XI:

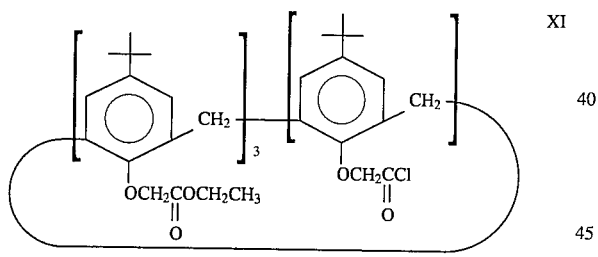

(0.0031 mole) which was dissolved in 5 mls dry THF, then added to 0.76 g (0.0045 mole) 3-hydroxy-4-nitrobenzyl alcohol and 0.27 mls (0.0045 mole) triethylamine in 10 mls dry THF. The reaction mixture was allowed to stir for 24 hours at room temperature, after which all volatiles were removed and the product taken up in 50 mls dichloromethane which was washed twice with water, then dried over magnesium sulphate and filtered. The dichloromethane was then removed under reduced pressure to give 2.65 g (784 yield) pale brown title product (Ligand 2) which was purified by column chromatography on silica employing 25% 40°–60° C. petroleum ether/dichloromethane as eluent to give 1.8 g (67%) pale brown pure product mp 117°–119° C. i.r. spectroscopy results: v 1752 (S) C=0 cm$^{-1}$ Elemental Analysis results (calculated for $C_{65}$ $H_{81}$ $NO_{15}$ C=69.93, H=7.31, N=1.26. Found C=69.51, H=7.24, N=1.17%) The monochromogenic tetramer compound is in cone conformation, as confirmed by NMR. results: $^1$H NMR CDCl$_3$ RT. 2 t-butyl resonances 1.16 S area 27 H, 1.00 S area 9 H ppm

EXAMPLE 3

Preparation—Ligand 3 (formula XII)

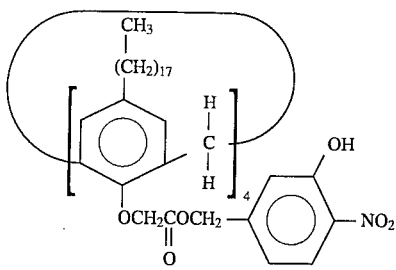

5,11,17,23,Tetra-n-octadecyl-1 25,26,27,28-tetra(3-hydroxy-4-nitro)benzyloxycarbonylmethyleneoxycalix[4]arene The reaction mixture consisted of 0.05 g (0.35 mmol) p-n-octadecylcalix[4]arene, prepared following the method described by Nakamoto et al.$^{30}$ 0.29 g (2.1 mmol) anhydrous potassium carbonate, 0.47 g (2.8 mmol) ethyl bromoacetate and 15 mL anhydrous acetone. This was refluxed under nitrogen for 96 hours, after which all volatiles were removed at room temperature. The resulting residue was taken up in 25 mL dichloromethane and 25 mL 1M aqueous HCl. The organic layer was separated, dried and volatiles removed to give 0.65 g pale brown solid tetraethylester calix[4]arene, which was chromatographed on neutral alumina using 50% pet. ether—methylene chloride as eluant to give 0.37 g (60%) of tetraethylester calix[4]arene (formula XIIa) as a very pale brown solid, m.p. 49°–51° C.[Found: C, 74,74%;H,10,04%; $C_{116}H_{192}O_{12}$. $CH_2Cl_2$ requires C,75.40%;H,10.41%]; $v_{max}$ (KBr/cm$^{-1}$):1757(S)(broad, C=0).

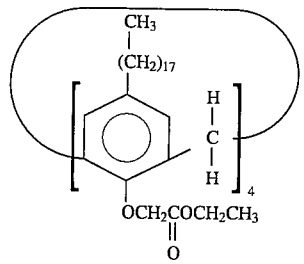

All (0.37 g) of this compound was then refluxed for two hours with 0.40 g (7.1 mmol) potassium hydroxide in 5 mL ethanol, after which all volatiles were removed. To the residue was then added 5 mL of 10M aqueous HCl to give a colourless solid which was then washed well with distilled water and left to dry at room temperature for 72 hours to give 0.35 g of colourless carboxylic acid (m.p. 68°–71° C. $v_{max}$ KBr/cm$^{-1}$ 1737(S) C=0). This compound was refluxed under nitrogen with 5 mL thionyl chloride for 2 hr. after which all volatiles were removed to give 0.36 g grey solid acid chloride. This amount of tetraacid chloride (0.2 mmol) was dissolved in dry THF (5 mL) and added dropwise under nitrogen with stirring to 3-hydroxy-4-nitrobenzyl alcohol (0.15 g 0.9 mmol) and triethylamine (0.12 mL, 0.9 mmol) in THF (5 mL). The mixture was stirred at room temperature for 24 hr. at which stage all volatiles were removed. The resulting residue was dissolved in methylene chloride (10 mL) and 1M HCl (5 mL). After washing twice with distilled water, the organic layer was separated, dried and volatiles removed to give 0.46 tetra (3-hydroxy-4 nitro) benzyl ester (Ligand 3—formula XII)). Pure product Ligand 3—formula XII) was obtained as a yellow solid (m.p. 64°–5° C.) by chromatography on neutral alumina using 15% pet ether-methylene chloride as eluant 0.40 g (87%). [Found: C, 70.92%; H, 8.47%; N, 2.13%. $C_{136}H_{196}N_4O_{24}1/2CH_2Cl_2$ requires C,70.86%; H,8.58%; N,2.42%]; $v_{max.}$ (KBr/cm$^{-1}$): 3500 (OH), 1753(S) C=0. 1465 (NO$_2$).

EXAMPLE 4

Preparation—Ligand 4 (formula XIII)

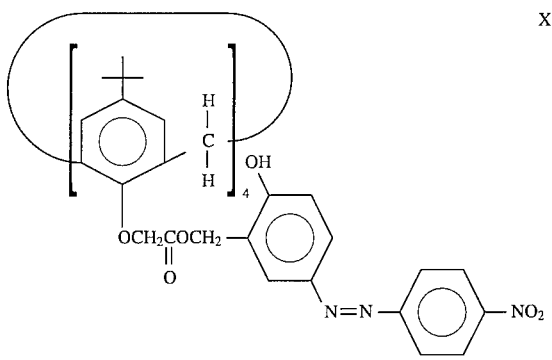

XIII

To 2.2 g (0.0025 mole) tetra p-tert-butylcalix[4]arene tetraacetic acid prepared as in EP 0 237 265 Harris assigned to Loctite (Ireland) Ltd was added 6.7 mls thionyl Chloride and the entire was stirred under reflux for 2 hrs. All volatiles were then removed to give 2.4 g colourless tetraacetyl chloride.

1.2 g (0.00122 mole) of this compound was dissolved in 5 mls dry THF under nitrogen to which was added 1.5 g (0.0055 mole)2-hydroxy-5(4'-nitrophenylazo) benzyl alcohol and 0.44 g(0.0055 mole) pyridine in 5 mls dry THF with stirring. The red-brown reaction mixture was then allowed to stir for 24 hours at room temperature after which all volatiles were removed then taken up into 25 mls dichloromethane which was washed once with 5% aqueous HCL then water to give after drying with magnesium sulphate 2.2 g (95%) red-brown solid. Chromatography on neutral alumina employing dichloromethane as eluent furnished title product 1.76 g(80%) mp 111°–115° C. i.r.-spectroscopy results: v 1740 (S) C=0 1600 m N=N Elemental Analysis results (calculated for $C_{104}H_{96}O_{24}N_{12}$ C: 65.81, H: 5.10. Found C: 65.62, H=5.60%)

The compound (formula XIIIa)

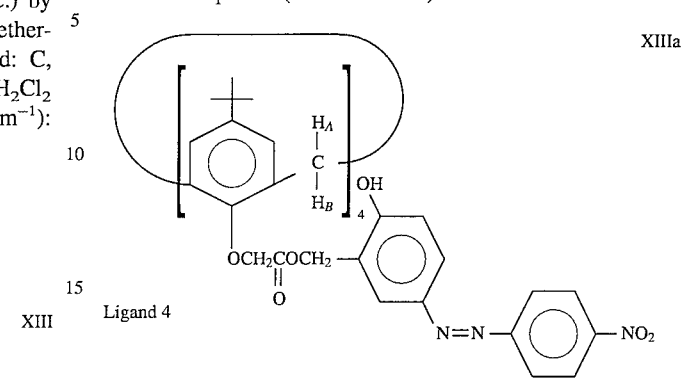

Ligand 4 is in distorted cone conformation as shown by resonances in $^1$HNMR CDCl$_3$RT

Complex t-butyl region between 0.9 and 1.3 ppm. Upon complexation with NaSCN they collapse to one singlet 1.2 ppm.

EXAMPLE 5

Preparation-Ligand 5 (formula XIV)

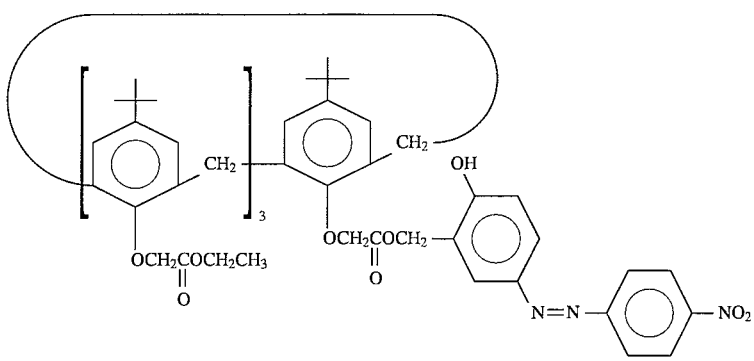

XIV 1.0 g of the triester monoacid chloride XI from Example 2 (0.001 mole) was dissolved in 5 mls dry THF then added to 0.419 (0.0015 mole) 2-hydroxy-5(4'-nitrophenylazo) benzyl alcohol and 0.129 (0.0015 mole) dry pyridine in 10 mls dry THF. The reaction mixture was allowed to stir at room temperature for 24 hours after which all volatiles were removed and the product taken up in 25 mls dichloromethane which was washed once with 5% aqueous HCL, then water, then dried over magnesium sulphate to give 1.29 (98%) pale red-brown solid. Chromatography on neutral alumina utilising dichloromethane as eluent gave 0.859 (70%) title product (Ligand 5—formula XIV) as a pale red-brown solid mp 60°–64° C. i.r. Spectroscopy results: v 1752 (S) C=0(OCH$_2$CH$_3$), 1740 sh (M)C=0 (OCH$_2$ Ph), 1600 (M) N=N. Elemental Analysis results (calculated for C$_{71}$H$_{84}$O$_{15}$N$_3$=66.29, H=6.65, N=3.22 Found C=66.33, H=6.51, N=3.00%).

EXAMPLE 6

Preparation—Ligand 6 (formula XV)

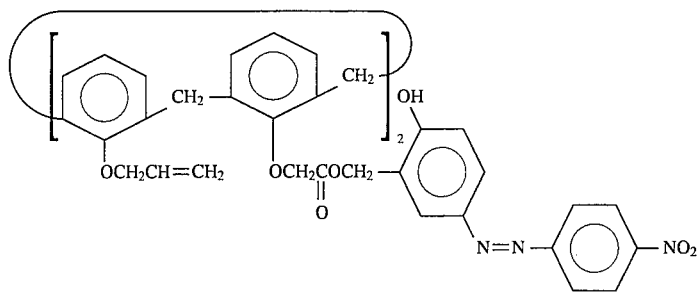

Treatment of Calix-4-arene with two equivalents of allyl bromide in the presence of anhydrous K$_2$CO$_3$ in acetonitrile following the method of Van Loon et. al. Tetrahedron Letters 30 (20) 1989 p 2681 gave Compound XVI:

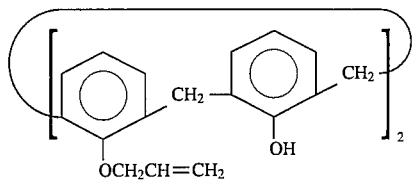

in 72% yield. This compound in turn was treated with ethyl bromoacetate and anhydrous K$_2$CO$_3$ in acetone following the method of U.S. Pat. No. 4,642,362 Harris et al assigned to Loctite (Ireland) Ltd and gave Compound XVII:

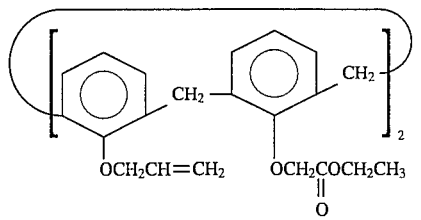

in 75% yield. This compound in turn was hydrolysed with ethanolic KOH followed by acidification with HCL following the method of EP 0309291A1 Harris et al assigned to Loctite (Ireland) Ltd to give Compound XVIII:

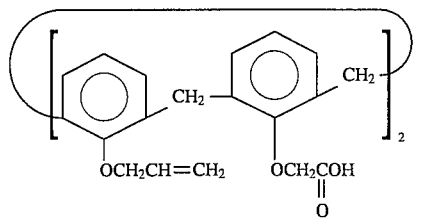

in 94% yield. 1.0 g (0.0016 mole) of this compound was refluxed with 5 mls thionyl chloride for 2 hours under nitrogen to give after removal of all volatiles under vacuum 1.03 g (100%) yield Compound XIX:

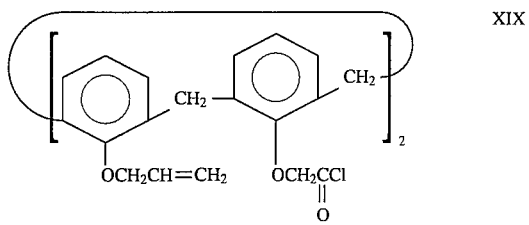

This compound was dissolved in 5 mls dry THF under nitrogen to which was added 0.87 g (0.0032 mole) 2-hydroxy-5 (4'-nitro phenylazo) benzyl alcohol and 0.26 g (0.0032 mole) dry pyridine in 5 mls dry THF with stirring. The reaction mixture was stirred for 24 hours at room temperature after which all the volatiles were removed then taken up in 20 mls dichloromethane which was washed once with 5% aqueous HCL then water to give after drying over dried magnesium sulphate 1.6 (89% yield) red-brown solid. Chromotography on neutral alumina utilising dichloromethane as solvent gave 1.3 g (72%) title product (Ligand 6—formula XV) as a red-brown solid mp 65°–8° C. i.r. Spectroscopy results v 1740(S) C=0 1600 (M) N=N Elemental Analysis results (calculated for C$_{64}$H$_{52}$O$_{14}$N$_6$=C=68.08, H=4.64, N=7.44, Found C=67.74, H=4.54, N=7.10%).

Experimental

Materials

Tetrahydrofuran (THF) was obtained from Fluka Chemika (Examples 7–8) or Aldrich Chemical Company (Example 9). Butan-1-ol and triethylamine (TEA) were purchased from Riedel De Haen. Deuterated chloroform, sodium thiocyanate, morpholine, and the perchlorates of lithium, sodium and potassium were obtained from the Aldrich Chemical Company. Tridodecylamine (TDDA) was obtained from Aldrich Chemical Company (Examples 7–8) or from BDH Chemicals (Examples 9). The perchlorate solutions were made up in Milli-Q water. NMR, IR and UV-VIS spectra were obtained with Bruker AC-400 spectrometer, a Perkin-Elmer 983G spectrophotometer, and a Hewlett-Packard 8452A Diode Array Spectrophotometer, respectively.

BRIEF DESCRIPTION OF DRAWINGS

In the accompanying drawings

EXAMPLE 7

Effect of Complexation on UV-VIS Absorbance
(Ligands 1–3)

Solutions of the ligands were made up in THF, (ligand 1 and 3 at $5 \times 10^{-5}$M, and ligand 2 at $10^{-4}$M). 2.5 mL aliquots of these solutions were taken and liquid morpholine was added in the following amounts, 20 ul for ligands 1 and 3, 45 ul for ligand 2. Incremental concentrations of the aqueous metal perchlorates were added to give final concentrations in the range $10^{-1}$ to $10^{-6}$M. The UV-VIS spectra of the solutions were obtained between 800 and 300 nm. In order to determine selectivity coefficients in this one phase system, a series of experiments was set up as above, with the final lithium perchlorate concentration being varied in the range $10^{-1}$ to $10^{-6}$M, in a fixed background concentration i.e. $10^{-2}$ or $10^{-3}$M, of interfering ion in the form of sodium perchlorate. Spectra were obtained from 800–300 nm.

Figure 1A:
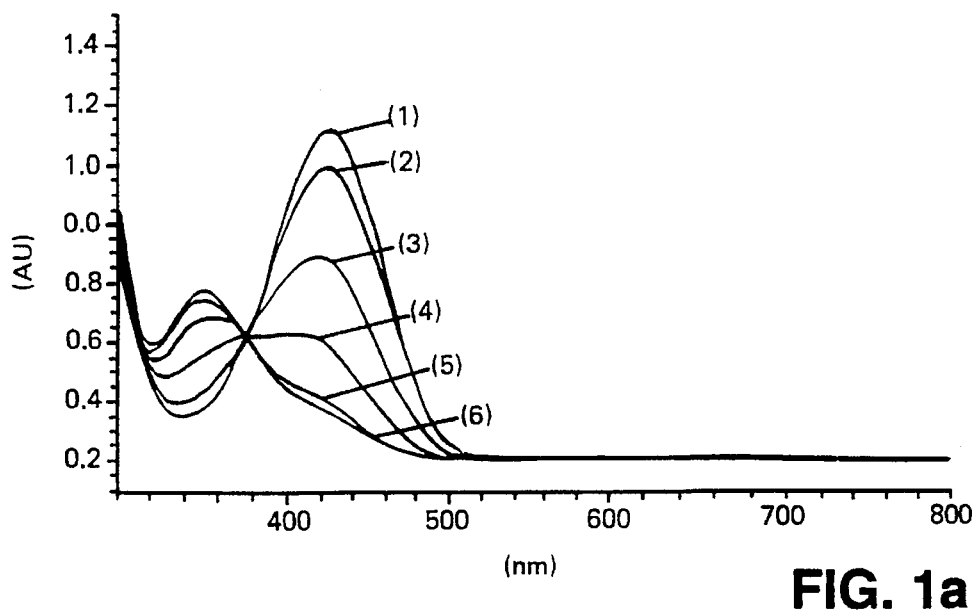
FIGS. 1(a)–(c) are graphs of instrument data for Absorbance (AU) against Wavelength (nm) from a one phase investigation of changes in the absorbance spectrum of 2.5 ml of a 5×10$^{-5}$M solution of (a) ligand 1, and (c) ligand 3 in THF, with 20 ul morpholine, and (b) 10$^{-4}$M ligand 2 in THF, with 45 ul morpholine, upon addition of aqueous $LiClO_4$, with final concentrations of 0.1M (1), $10^{-2}$M (2), $10^{-3}$M(3), $10^{-4}$M (4), $10^{-5}$M (5), $10^{-6}$M (6), OM (7).
Figure 1B:
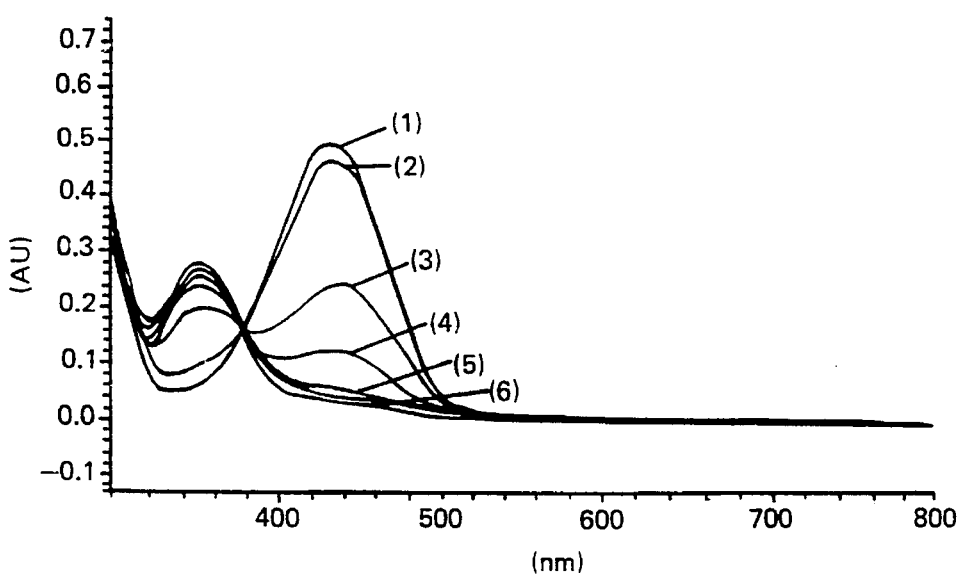
Figure 1C:
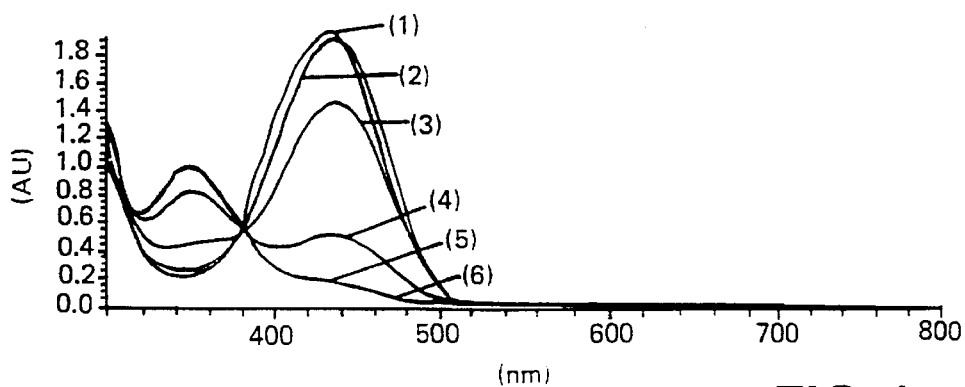

A number of parameters should be considered when setting up experiments involving these types of chromogenic calixarenes. The base must not be too strong, or deprotonation of the chromogenic group attached to the calixarene will occur in the absence of the metal ions. With the base morpholine a slight colour change in tetrahydrofuran was noticed after the addition of base, indicating that the bulk of the ligand remained in the protonated form in both cases. The UV-VIS spectrum of the ligand in THF with morpholine before the addition of $LiCLO_4$, is shown as the lowest trace in FIG. 1(a), 1(b) and 1(c) confirming that very little deprotonation has occurred.

Upon addition of lithium perchlorate in the presence of morpholine to the colourless solutions of ligands 1, 2 and 3 in THF, a clear yellow colour was immediately observed, with the density of the colour being dependent on the concentration of the metal perchlorate added. From the UV-VIS spectra, (FIGS. 1a to 1c), an absorbance maximum for the coloured complex at 425 nm and an isobestic point at 375 nm can be clearly identified. The chromogenic calixarene, which is slightly acidic in nature due to the presence of the nitro phenol group on the chromogenic moiety, can undergo complexation in the absence of base. This produces the complexed form of the calixarene, which is more acidic than its uncomplexed analogue due to the presence of the positive charge of the metal ion residing in the polar cavity defined by the carbonyl oxygen atoms. In the system investigated, the bases are able to deprotonate the nitrophenol group of the ion-calixarene complex, but not of the uncomplexed calixarene. The nitrophenolate group in the complex may be electrostatically associated with the complexed cation in the form of an internal salt.

Figure 2A:
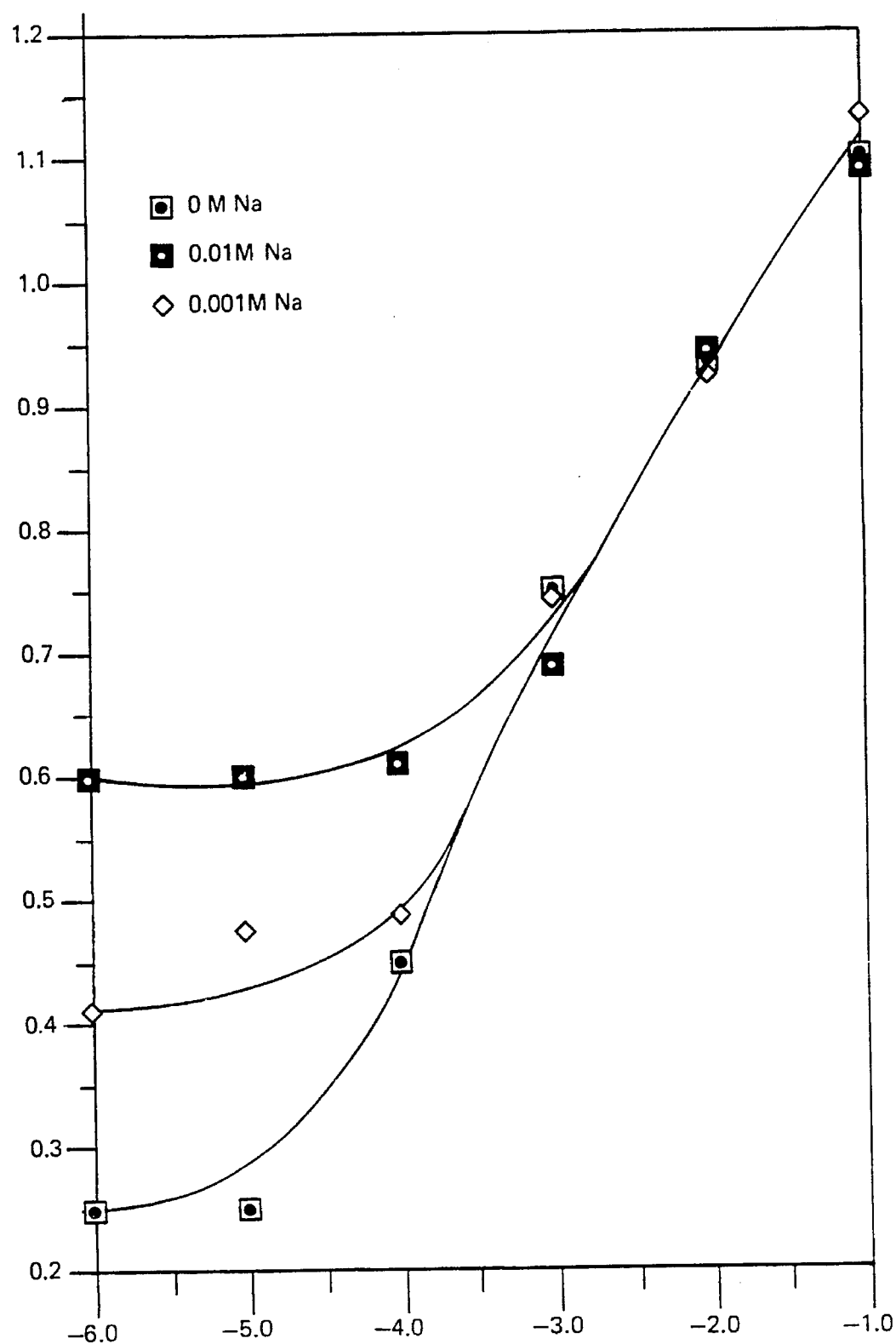
FIGS. 2(a)–(c) are graphs of Absorbance (AU) at 425 nm against log (Li)/mol $dm^{-3}$ from one phase studies of the optical response of (a) $5 \times 10^{-5}$M ligand 1 in THF with 20 ul morpholine; (b) $10^{-4}$M ligand 3 in THF with 45 ul morpholine; (c) $5 \times 10^{-5}$M ligand 2 in THF with 20 ul morpholine; to additions of $Li^+$ in the presence of fixed concentrations of sodium perchlorate.
Figure 2B:
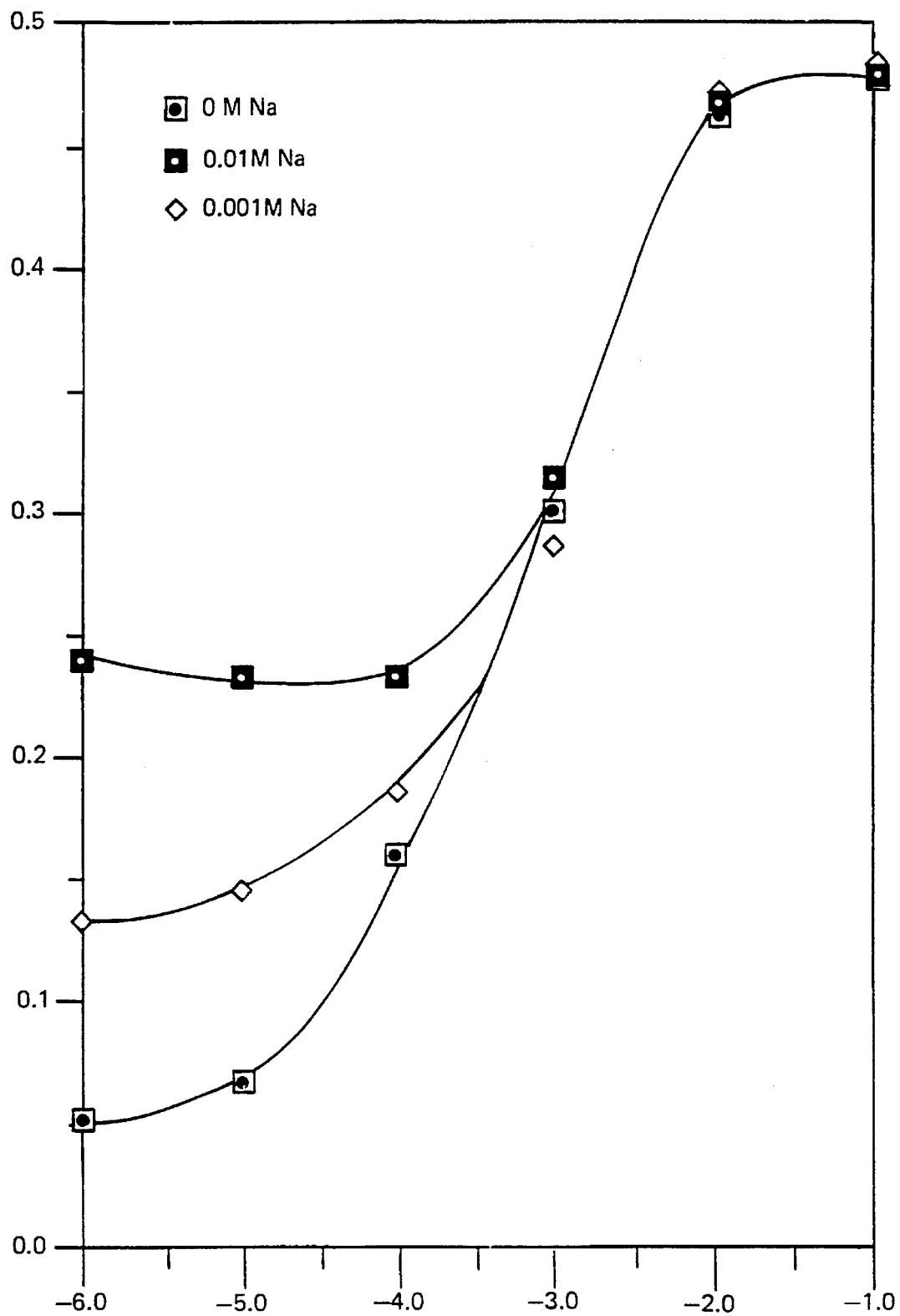
Figure 2C:
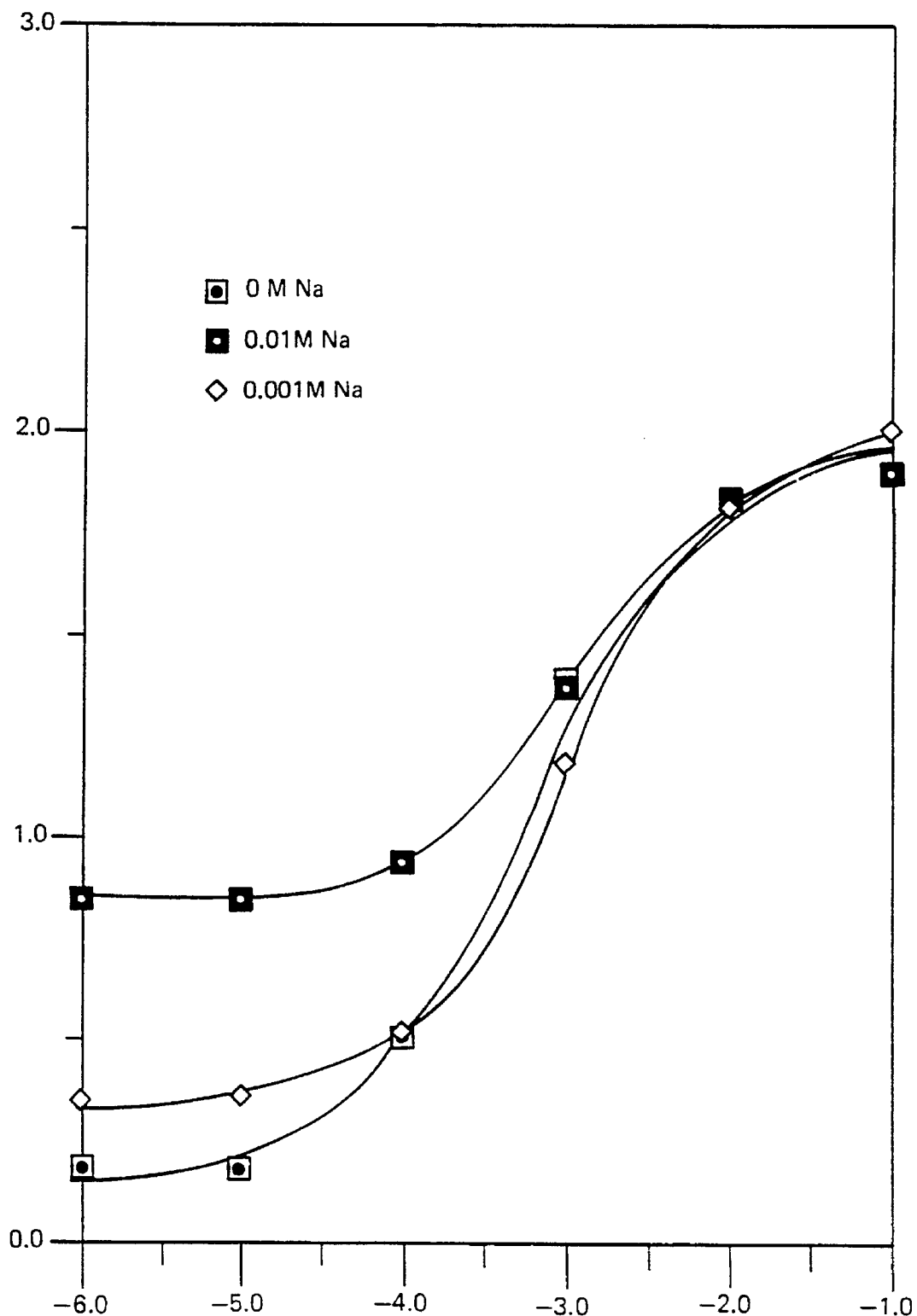

The colour and spectral changes observed upon the metal complexation with the monochromogenic ligand 2 suggest that one deprotonation is sufficient for a colorimetric response to be observed, as only one labile proton is available per molecule, in contrast to ligand 1 which has four. The interference studies carried out using fixed concentrations of sodium perchlorate interferent are illustrated in FIGS. 2a, 2 and 2c. From the intercept between the lithium response curve and the sodium interference curve, selectivity coefficients were estimated. An approximate selectivity coefficient ($K_{Li, Na}$) can be calculated from the concentrations of the ions at the intercept via the expression $K_{Li, Na} = C_{Na}/C_{Li}$ (See Table 1)

TABLE 1

| Ligand | 1 | 1 | 3 | 3 | 2 | 2 |
| --- | --- | --- | --- | --- | --- | --- |
| [$Na^+$] | $10^{-2}$ | $10^{-3}$ | $10^{-2}$ | $10^{-3}$ | $10^{-2}$ | $10^{-3}$ |
| $K_{Li, Na}$ | 25.1 | 11.2 | 43.1 | 23.2 | 34.7 | 14.7 |

Ligand 2 was found to be slightly more selective for lithium than ligand 1, with selectivity coefficients of 34.7 and 25.1 against $10^{-2}$M sodium and 14.7 and 11.2 against $10^{-3}$M sodium, calculated for lithium against sodium for ligand 1 and ligand 2 respectively.

EXAMPLE 8

Effect of Complexation on UV-VIS Absorbance
(Ligands 4–6)

$5 \times 10^{-5}$M solutions of ligands 4 and 5 and a $6 \times 10^{-5}$M solution of ligand 4, were made up in THF. 2.5 mL aliquots of each ligand solution were taken and to this 100 uL of tri-n-dodecylamine was added. Incremental concentrations of aqueous lithium perchlorate were added to give final metal perchlorate concentrations of $10^{-6}$M, to 0.1M. After gently shaking, the clear yellow ligand solution changed colour to red immediately, with the intensity of the resultant colour being dependent on the metal perchlorate concentration. This colour change was examined using UV-VIS spectroscopy in the range 300–800 nm (FIGS. 3(a)–(c)).

In order to determine selectivity coefficients for lithium against sodium, a series of experiments was set up as above, with the final lithium perchlorate concentration being varied in the range $10^{-6}$ to $10^{-1}$M, in a fixed background concentration of interferent (0.05M and 0.1M sodium perchlorate). Spectra were obtained from 300–800 nm and graphs of absorbance at 520 nm versus the log of the concentration of lithium perchlorate drawn (see for example FIG. 4a, 4b and 4c). At high concentrations, the sodium ion has the effect of reducing the response of the ligand to lithium at lower concentrations as it dominates the complexation process with the ligand and swamps any lithium ion effects. However, at higher lithium ion concentrations, a response will be observed because of greater affinity of the ligand for lithium ions. From these graphs, selectivity coefficients can be estimated from the ratio of the sodium and lithium ion concentrations at the intersection of the sodium and lithium dominant response regions of the curves.

Figure 3A:
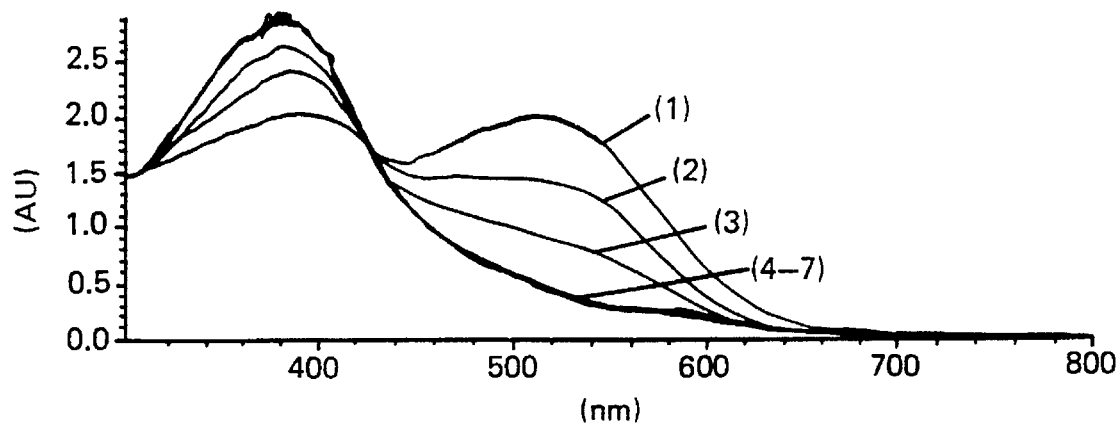
FIGS. 3(a)–(c) are graphs of Absorbance (AU) against wavelength (nm) from a one phase investigation of changes in the absorbance spectrum of 2.5 mL of solutions of (a) $5.0 \times 10^{-5}$M ligand 4 and (b) $5.0 \times 10^{-5}$M ligand 5 and (c) $6.0 \times 10^{-5}$M ligand 6 in THF with 100 ul of TDDA, upon addition of aqueous lithium perchlorate, with final lithium concentrations of: 0.1M (1), $10^{-2}$M (2), $10^{-3}$M (3), $10^{-4}$M (4), $10^{-5}$M (5), $10^{-6}$M (6).
Figure 3B:
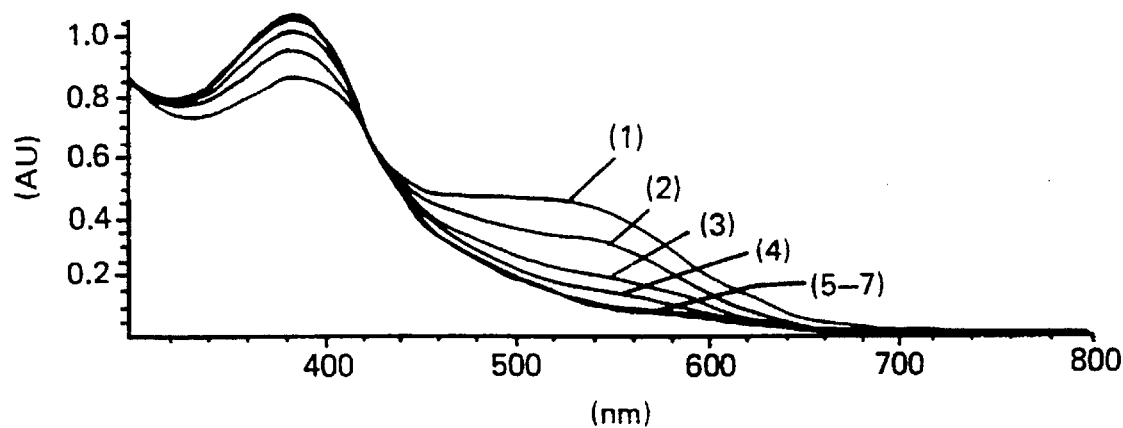
Figure 3C:
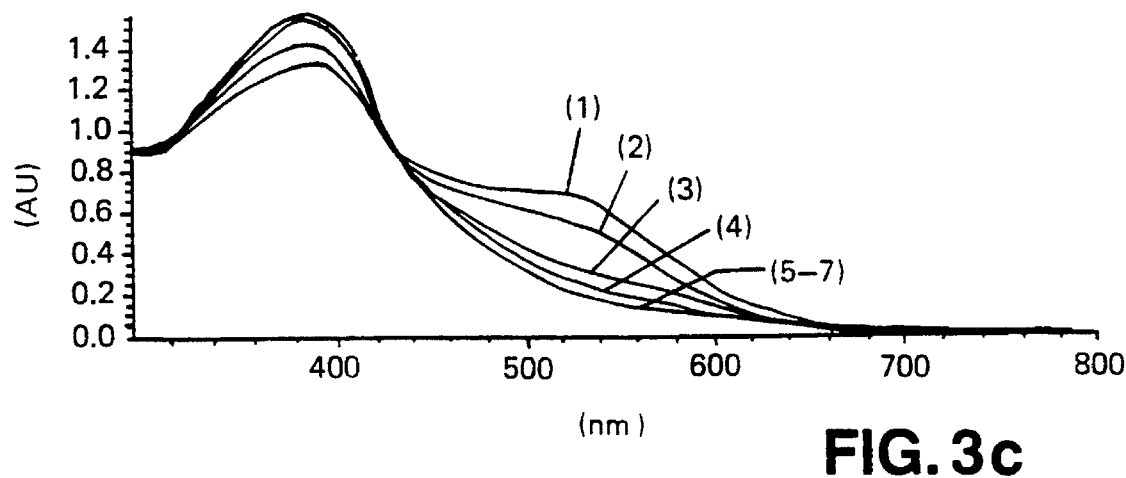

A slight colour change from yellow to bronze was noted upon the addition of the TDDA to the solution. This effect coincided with an increase in absorption at the uncomplexed wavelength absorbance maximum at 380 nm. No increase in intensity at 520 nm was noted. FIGS. 3a, 3b, and 3c illustrate the effect of varying lithium perchlorate concentration on the absorbance spectrum of ligands 4, 5 and 6 respectively. As anticipated complexation led to a shift in $_{max}$ from 380 nm to 520 nm with a isobestic point at 425 nm, and the increase in the absorbance at 520 nm being dependent on the concentration of lithium perchlorate. No colour change was observed in the absence of the base. This is indicative of the deprotonation of the azophenol group upon metal ion complexation being the cause of the colour change, as the presence of the base facilitates the removal of the phenolic proton.

Figure 4A:
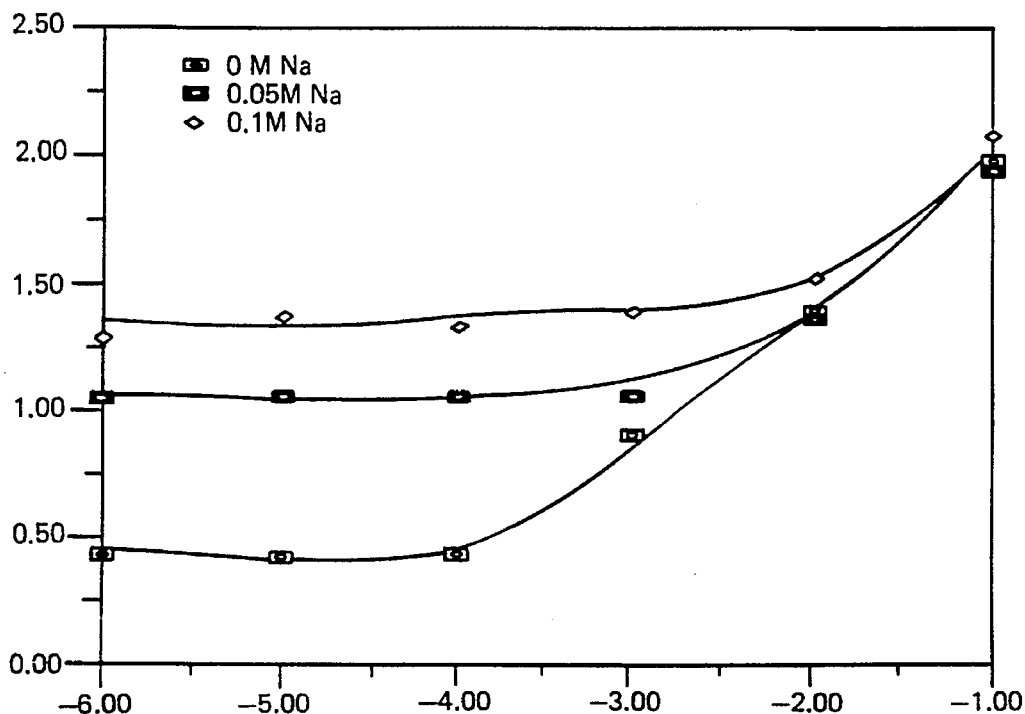
FIGS. 4(a)–(c) are graphs of Absorbance at 520 nm against log (Li)/mol $dm^{-3}$ from one phase studies of the optical response of $5.0 \times 10^{-5}$M solutions of: (a) $5.0 \times 10^{-5}$M ligand 4 and (b) $5.0 \times 10^{-5}$ ligand 5 and (c) $6.0 \times 10^{-5}$M ligand 6, in THF with 100 ul of TDDA, with varying concentrations of lithium perchlorate in the presence of fixed concentrations of sodium perchlorate.
Figure 4B:
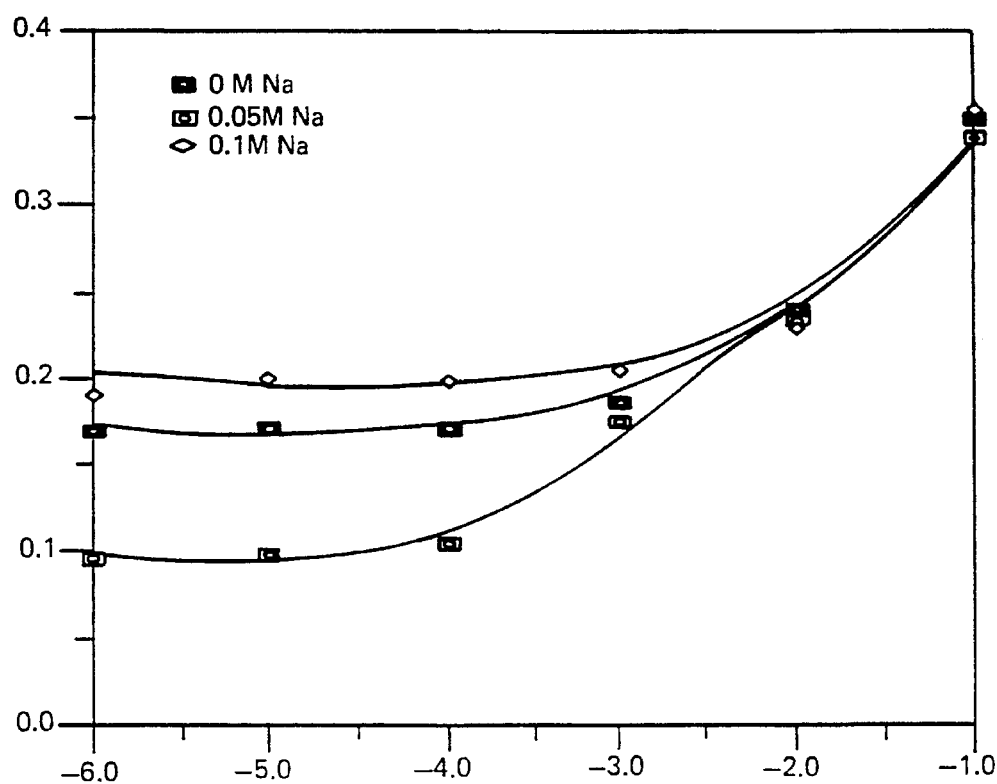
Figure 4C:
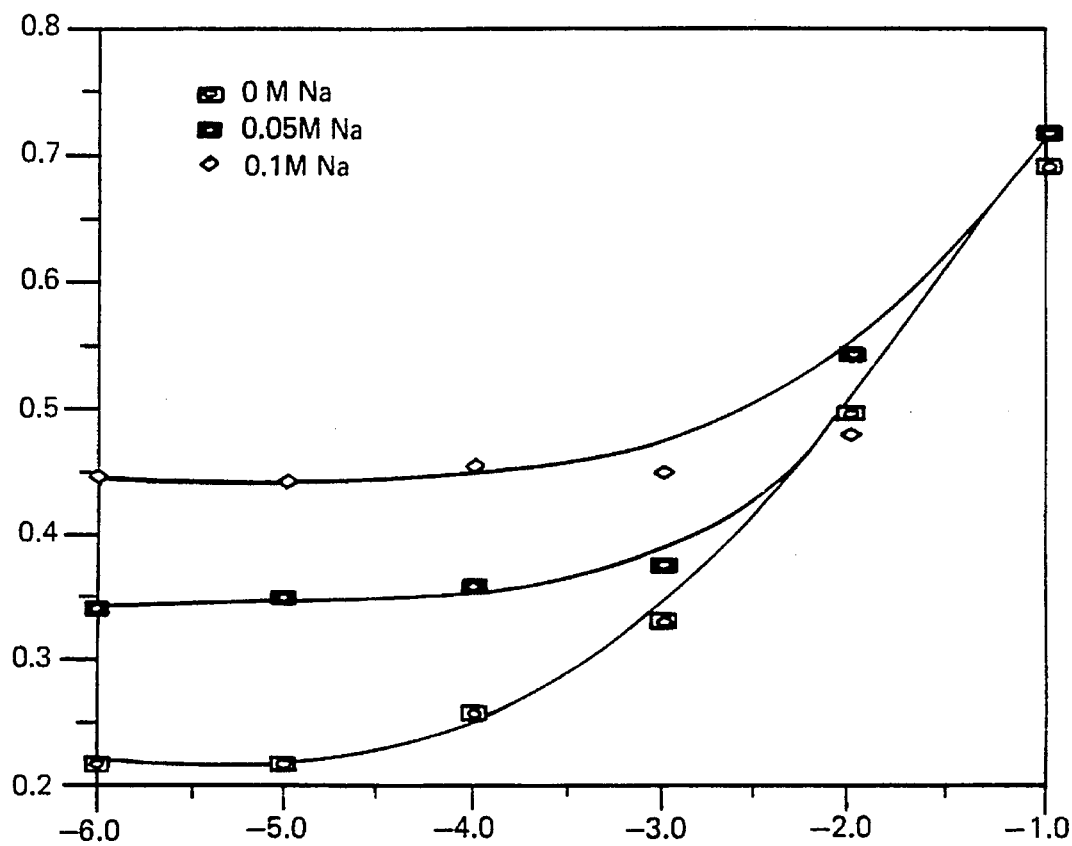

FIGS. 4a, 4b, and 4c shown the absorbance at 520 nm versus log lithium perchlorate concentration for ligands 4, 5 and 6 respectively at each level of sodium perchlorate interferent. The monochromogenic ligand, ligand 5 displayed the best lithium against sodium selectivity. Selectivity coefficients of 73.5, 50.0 and 31.6 against 0.05M sodium and 73.3, 36.8 and 31.5 against 0.1M sodium for ligand 5, 6 and 4 respectively were estimated. These values are an improvement on those obtained with the nitrophenol ligands (Example 7). When potassium perchlorate was used as the complexing metal, no colour/spectral change was observed until a final concentration of potassium perchlorate of 0.1M had been added, suggesting that all three ligands are very selective against this metal ion.

EXAMPLE 9

Assessment of a chromogenic calixarene (Ligand 4) for the rapid colormetric detection of Trimethylamine (TMA).

Figure 5:
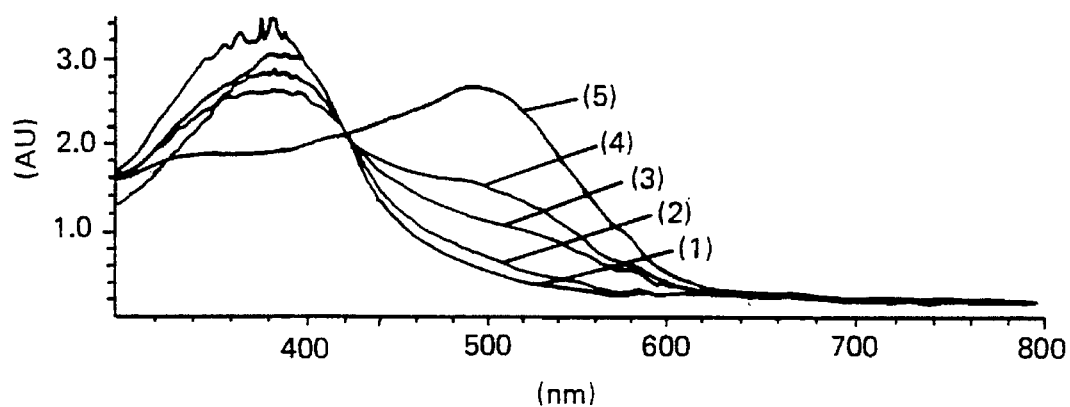
FIG. 5 is a graph of Absorbance (AU) against wavelength (nm) from an investigation of changes in the absorbance spectrum of a 2.5 mL solution of $5 \times 10^{-5}$M ligand 4 with 1M lithium perchlorate in butanol, upon exposure to gaseous TMA in the following concentrations, (1). 0 ppm, (2) 0.45 ppm, (3) 2.25 ppm, (4) 4.88 ppm, (5) 22.50 ppm.

Amine Detection (a) Liquid-Phase Experiments 2.5 mL of a solution containing $5\times10^{-5}$M of ligand 4 and 1M $LiClO_4$ in butanol was placed in a test tube in a gas tight vessel. Fixed volumes between 0.2 and 50 uL of a 25% aqueous TMA solution were injected into a 550 mL capacity vessel through a supa seal cap, ensuring that none of the liquid entered the test tube containing the indicator solution, giving final TMA concentrations in the approximate range of 0.1 to 25.0 ppm assuming all TMA passes into the gas phase. The vessel was heated gently in a 50° C. oven to aid the evolution of TMA from the aqueous solution into the gaseous form. After reaction, samples of the solution were removed in order to obtain the UV-VIS spectra (FIG. 5).

On release of the TMA inside the gas tight vessel, the colour of the indicator solution changed from yellow to red with the colour density and time taken for colour development both being dependent on the TMA concentration. The time taken for colour development ranged from under ten seconds for concentrations above 4.5 ppm to three hours for 0.45 ppm. These colour changes were measured using UV-VIS spectroscopy where an increase in absorbance at 490 nm (from the deprotonated form of the complexed calixarene) and a decrease in absorbance at 376 nm (from the protonated form of the complexed calixarene) in butanol was noted. FIG. 5 shows changes in the UV-VIS absorbance spectrum of the complexed calixarene solution to varying concentrations of gaseous TMA. Using this instrumental approach, a sub-ppm limit of detection is evident. Above approximately 30 ppm TMA no further discernable colour or spectral change could be obtained, with the solution being a deep reddish colour at this level.

(b) Test Strips based on Ligand 4

Using a filter paper disc (Watman no. 1–1.0 cm radius) as the support, the complexed calixarene was immobilised by spotting a tetrahydrofuran (THF) solution which was $5\times10^{-5}$M in ligand 4 and 0.1M in $LiClO_4$ onto the paper. Evaporation of the THF yielded a paper with a yellowish tinge. The $LiClO_4$ concentration in these experiments was reduced to 0.1M since it was impossible to dissolve the quantity required to give a 1M solution of the perchlorate in THF, which had been previously shown to give a dramatic colour change upon complexation with Ligand 4 in the presence of a base. Test strips prepared in this manner were placed in a gas-tight vessel of capacity 2.71 L, and varying volumes of TMA were injected through a supa seal cap to give a final TMA concentration of 0.010 to 50 pp million. Striking colour changes from yellow through peach to pink-red were noted on the test strips for concentrations above 0.020 ppm, with a detectable difference in colour observed for TMA concentrations in the range 0.020 and 30 ppm (FIG. 4). In one particular test at a concentration of 1.0 ppm TMA a clear colour change from yellow to red-brown was observed while a control strip subjected to exactly the same conditions as the test strip but without exposure to TMA remained yellow. Above 30 ppm no further change in colour density was visually discernable. Full colour development occurred very quickly after the introduction of TMA into the gas tight system, with the lowest concentrations producing a colour change in under two minutes, and shorter times being observed for higher concentrations. The process is completely reversible, and test strips left in air returned to their original form within several minutes.

Covered Test Strips

Tests were subsequently carried out to determine whether the test strips could react to the presence of gaseous TMA when enclosed in a gas permeable membrane such as plastics packaging film of the kind known as "cling film". The test strips were prepared as before except that they were wrapped in cling film before being placed in the gas tight vessel. Visually no colour change was observed below 0.4 ppm TMA for exposure times of up to 8 hours. The development time decreased with increasing TMA concentration with full colour changes being observed after 20 minutes for 2.5 ppm TMA and almost instantaneous colour changes being observed above 10 ppm TMA.

Industrial Applicability

The invention provides chromoionophores which are industrially applicable in the manufacture of optical sensors, particularly for medical use.

The invention also provides a simple, sensitive colorimetric indicator for TMA which has potential use in the food industry particularly for the detection of spoilage in fish, and could be incorporated as a component in food packaging to indicate the onset of spoilage. The conditions of storage should be such that the amine is available in gaseous form. It was observed that the colour density is much greater and reaction times are much shorter for the test strips compared to the liquid phase experiments, despite a lower concentration of metal ions being available in the case of the case of the former (0.1 m $LiClO_4$ as compared to 1.0M $LiClO_4$). This is because in the liquid phase experiments, the experimental design is such that the amine must partition into the butanol phase and diffuse throughout it in order to generate the colour, whereas, with the test strip, only the coated surface of the paper is involved. Hence in the absence of any bulk diffusion processes, colour generation is much faster. In addition, as the ligand-metal mixture is not dispersed throughout a bulk liquid phase in the base of the test strips, but rather concentrated into a thin layer adhering to the paper surface, the density of the colour observed is much greater than for equivalent concentrations of TMA in the liquid phase experiments.

An extremely rapid and sensitive visual method for the detection of TMA between 0.02 and 50 ppm has been developed. Other substrates such as alumina thin-layer chromatography plates may be used in place of the filter paper. Although the depronation process is relatively non-selective, some degree of selectivity may be achieved on the basis of the $K_b$ value of the base through variation of $K_a$ of the ligand. This may be achieved through variation of the type and concentration of the metal ion co-immobilised with the ligand on the test strips. However, as a variety of volatile amines are evolved during fish spoilage, a broad-band indicator such as that reported above is more appropriate.

References

1. D. J. Cram, R. A. Carmack and R. G. Helgeson, J. Am. Chem. Soc., 110 (1988) 571.
2. R. C. Helgeson, B. P. Czech, E. Chapoteau, C. R. Gebauer, A. Kumar and D. J. Cram, J. Am. Chem. Soc. 111, (1989) 6339.
3. H. Shimizu, K. Iwamoto, K. Fujimoto, and S. Shinkai, Chemistry Letters, 1991. 2147–2150 (The Chemical Society of Japan).
4. K. Hiratini, J. Chem. Soc., Chem Comm. (1987) 960.
5. K. Hiratini, Analyst, 113 (1988) 1065.
6. T. Jin, K. Ichikawa, and T. Koyama, J. Chem. Soc. Chem Comm. (1992) 499.
7. R. J. Forster, A. Cadogan, M. Telting-Diaz, D. Diamond, S. J. Harris and A. M. McKervey, Sensors and Actuators B, 4 (1991) 325.
8. A. Cadogan, D. Diamond, M. R. Smyth, M. Deasy, A. M. McKervey and S. J. Harris, Analyst, 114 (1989) 1551.
9. H-G. Lohr and F. Vogtle, Acc. Chem. Res. 1985, 18, 65–72.
10. J. van Gent, E. & R. Sudholter, P. V. Lambeck, T. J. A. Popma, G. J. Gerritsma and D. N. Reinhoudt, J. Chem. Soc. Chem. Commun. 1988, 893
11. Y. Nakamoto, T. Nakayama, T. Yamagishi and S. Ishida, "Synthesis and Properties of Chromogenic Calixarene", Workshop on Calixarenes and Related Compounds, August 28–30, 1991, Johannes Gutenberg-Universitat, Mainz, Germany.
12. I. Aoki, H. Kawabata, K. Nakashima, and S. Shinka, "Fluorescent Calix(4)arene which responds to solvent polarity and metal ions", Workshop on Calixarenes and Related Compounds, August 28–30, 1991, Johannes Gutenberg-Universitat, Mainz, Germany.
13. S. J. Harris, M. A. McKervey, G. Svehla and D. Diamond, U.S. Pat. No. 5,132,345 issued July 21, 1992.
14. Sholl, A. F., Sutherland, I. O., J. Chem. Soc., Chem. Commun., 1992, 1716.
15. Misumi, S., Kaneda, T., J. of Inc. Phenom. and Molec. Rec. in Chem. 7, 1989, 83.
16. Van Gent, J., Sudholter, E J R., Lambeck, P. V., Popma, T. J. A., Gerritsma, G. J., Reinhoudt, D. N., J. Chem. Soc., Chem. Commun., 1988, 893.
17. Kaneda, T., Sugihara, K., Kamiya, H., Misumi, S., Tet. Lett, 1981, 22,44,4407.
18. Kubo, Y., Hamaguchi, S., Niimi, A., Yoshida, K., Tokita, S., J. Chem. Commun., 1993, 305.
19. King, M. A., Moore C. P., Samankumara Sandanayake, K. R. A., Sutherland, I. O., J. Chem., Soc., Chem. Commun., 1992, 583.
20. Simmonds, C. K., Lamprecht, E. C., 1985, in Microbiology of Frozen Foods (Ed. Robinson, R. K.), Elsevier Applied Science Publishers London and New York, pp 169–208.
21. Shewan, J. M., Mcintosh, R. G., Tucker, C. G., Ehrenburg, A. S. C., J. of Science of Food and Agriculture, 1953, 4, 283.
22. Dyer, W. J., J. of the Fisheries Research Board of Canada, 1945, 6, 351.
23. Dyer, W. J., J. of the Fisheries Research Board of Canada, 1950, 7, 576
24. Dyer, W. J., Journal of the Association of Official Agricultural Chemists, 1959, 42, 292.
25. Strachan, N. J. C., Nicholson, F. J., Int. J. Food Sc. and Tech., 1992, 27, 261.
26. Perez Martin, R. I., Franco, J. M., Molist P., Gallardo, J. M., Int. J. of Food Sc. and Tech., 1987, 22, 509.
27. Egashira, M., Shimizu, Y., Takao, Y., Chem. Lett., 1988, 389.
28. Egashira, M., Shimizu, Y., Takao, Y., Sens. Actuators, B1, 1990, 108.
29. Nakashima, K., Muraki, K., Nakatsuji, S., Akiyama, S., Kaneda, T., Misumi, S., Analyst, 1989, 114, 501.
30. Nakamoto Y., Kallinowski G., Boehmer V., Vogt W., Langmuir J., 1989 p.116–7

We claim:
1. A chromoionophore of formula IV

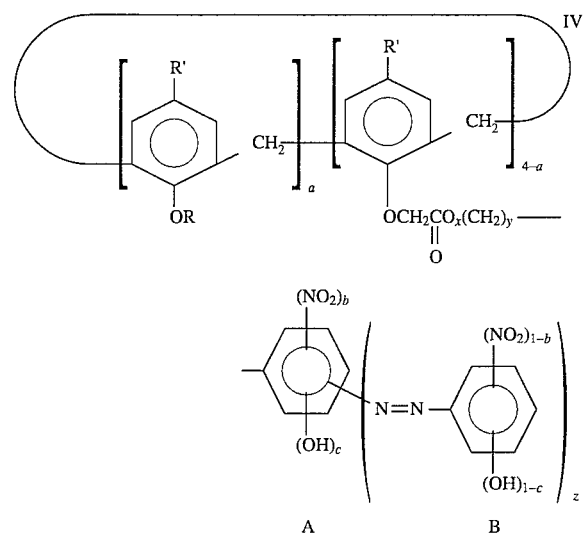

wherein
a=0–3,
b=0 or 1, c=0 or 1,
x=0 or 1,
y=0 or 1,
z=0 or 1,
provided that when Z=0, b=C=1, R', which is the same or different on each aryl group, is selected from H, halogen, aliphatic hydrocarbyl, aryl, aliphatic hydrocarbylaryl, and derivatives thereof selected from aliphatic hydrocarbyl, aryl and aliphatic hydrocarbylaryl substituted with one or more halo groups, substituted with one or more radicals containing nitrogen substituted by one or more oxo groups, or interrupted by one or more oxygen atoms.

2. A chromoionophore according to claim 1 wherein R is

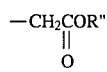

in which R" is selected from H, aliphatic hydrocarbyl, aryl, aliphatic hydrocarbylaryl, and derivatives thereof selected from aliphatic hydrocarbyl, aryl and aliphatic hydrocarbylaryl substituted with one or more halo groups, substituted with one or more radicals containing nitrogen, substituted by one or more oxo groups, or interrupted by one or more oxygen atoms.

3. A chromoionophore according to claim 1 wherein R is alkenyl.

4. A chromoionophore according to claim 2 which are of the formula V:

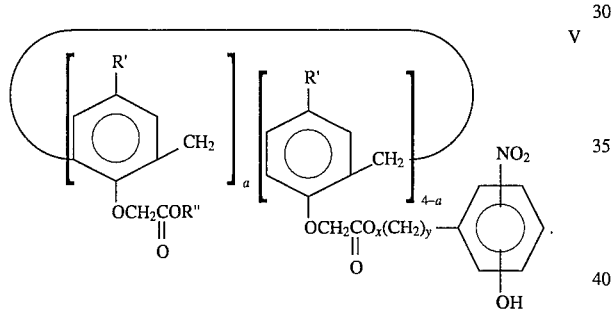

5. A chromoionophore according to claim 1 wherein the nitrophenol group is of the formula VI

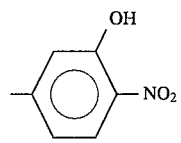

6. A chromoionophore according to claim 1, wherein x=y=1, b=0, c=1 and z=1.

7. A chromoionophore according to claim 6 wherein the nitrophenylazophenol moiety is of the formula XX

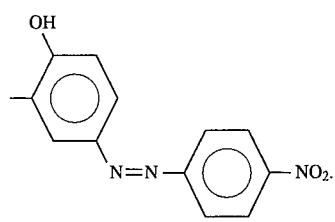

8. A chromoionophore according to claim 1 which is selected from compounds of the formulae VIII, IX, XII, XIII, XIV and XV

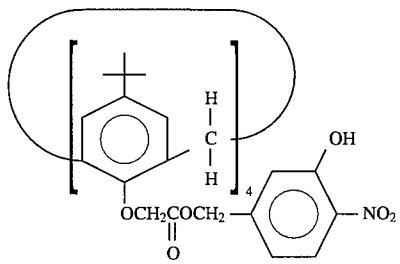

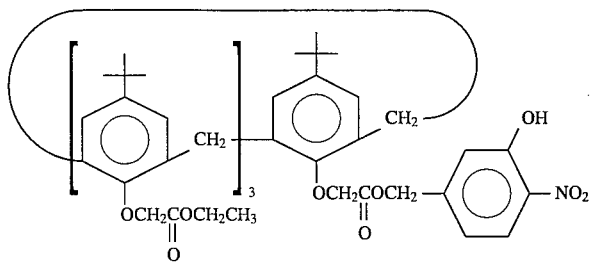

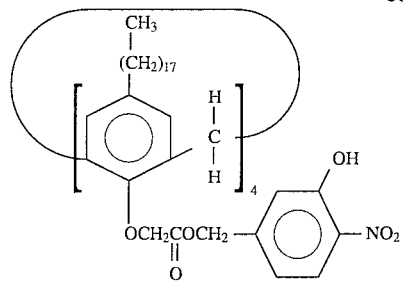

XII

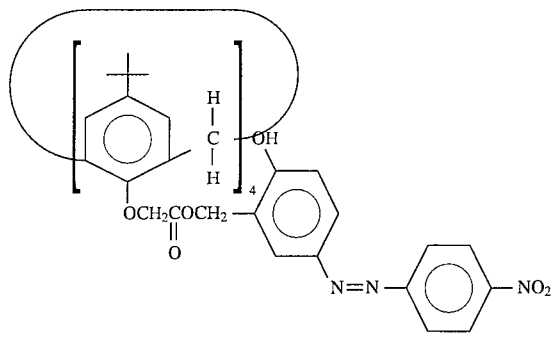

XIII

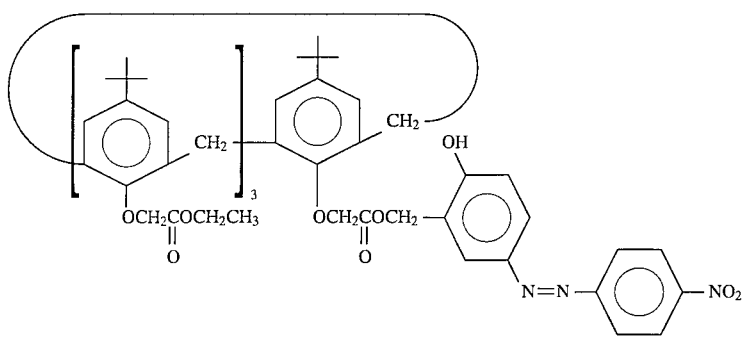

XIV

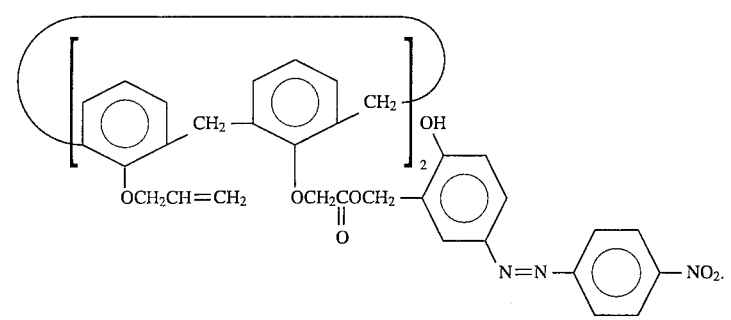

XV

9. An optical sensor comprising a chromoionophore according to claim 1 on a carrier suitable for an optical sensor.

10. An optical sensor according to claim 9 wherein the chromoionophore is complexed with an alkali metal cation.

11. An optical sensor according to claim 10 wherein the alkali metal cation is lithium.

12. An analytical method for determining alkali metal cations which comprises contacting a sample containing alkali metal cations with an optical sensor according to claim 9, in the presence of a base.

13. A method according to claim 12 for determining lithium.

14. A method for detecting the presence of a base which comprises locating an optical sensor according to claim 10 in an environment where the presence of a base is suggested.

15. A method according to claim 14 for detecting the presence of an amine.

16. A method according to claim 15 for detecting the presence of triethylamine.

* * * * *